United States Patent [19]

Cannon

[11] 4,204,538
[45] May 27, 1980

[54] CASSETTE FOR INTRAVENOUS CONTROLLER

[75] Inventor: Raymond E. Cannon, San Diego, Calif.

[73] Assignee: IMED Corporation, San Diego, Calif.

[21] Appl. No.: 913,282

[22] Filed: Jun. 7, 1978

[51] Int. Cl.² ............... A61M 5/00; A61M 5/21
[52] U.S. Cl. .................. 128/214 R; 128/214 F; 222/249; 222/386.5
[58] Field of Search ............... 128/231, 232, DIG. 12, 128/214 F, 214 R; 222/249, 386.5

[56] References Cited

U.S. PATENT DOCUMENTS

| 71,865 | 12/1867 | Fitzgeralds | 222/249 X |
|---|---|---|---|
| 1,782,704 | 11/1930 | Woodruff | 222/249 |
| 3,486,539 | 12/1969 | Jacuzzi | 128/DIG. 12 |
| 3,838,794 | 10/1974 | Cogley et al. | 128/214 F X |
| 3,894,538 | 7/1975 | Richter | 128/214 F X |
| 3,985,133 | 10/1976 | Jenkin et al. | 128/214 F |
| 4,041,944 | 8/1977 | Rhodes | 222/386.5 X |
| 4,112,947 | 9/1978 | Nehring | 128/DIG. 12 |
| 4,121,584 | 10/1978 | Turner et al. | 128/214 E |
| 4,142,523 | 3/1979 | Stegeman | 128/214 R |

Primary Examiner—Henry K. Artis
Attorney, Agent, or Firm—Ellsworth R. Roston

[57] ABSTRACT

A cassette provides for a controlled introduction of fluid from a source to a patient. It includes a block and a chamber in the block. Separating means such as a diaphragm are movable in the chamber to define first and second compartments each having a variable volume in accordance with such movement. A transducer is movable with the separating means. The transducer may include a coil disposed on the block and a magnetic rod magnetically coupled to the coil and movable with the separating means to vary the inductance of the coil.

Input and output lines are provided in the block. One of the lines in a first pair communicates with the input line and the first compartment and the other line in the first pair communicates with the second compartment and the output line. One of the lines in a second pair communicates with the input line and the second compartment and the other line in the second pair communicates with the first compartment and the output line. Control means provide alternately for a blocking of the second pair of lines and an opening of the first pair of lines and at other times for a blocking of the first pair of lines and an opening of the second pair of lines.

18 Claims, 9 Drawing Figures

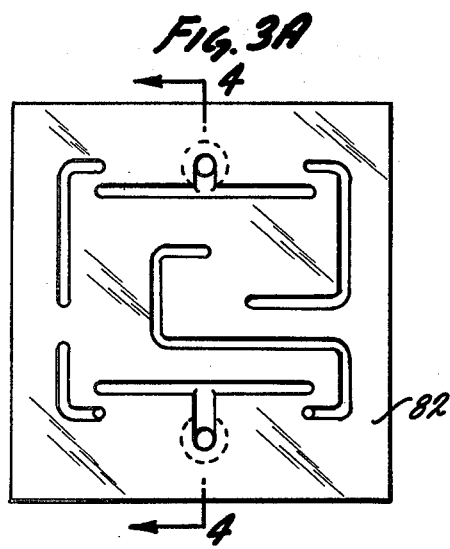
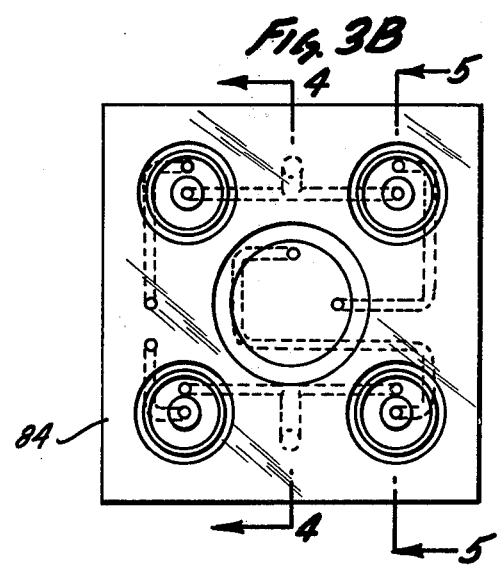
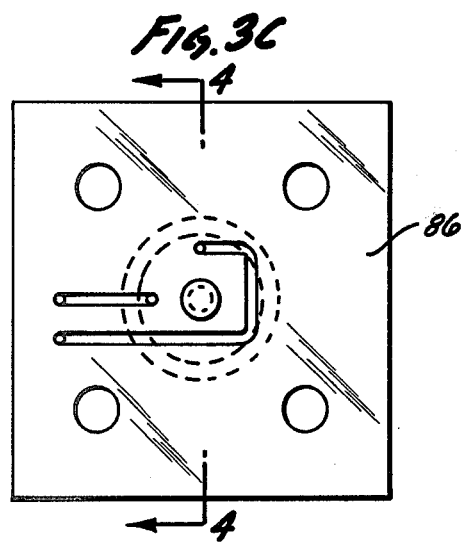
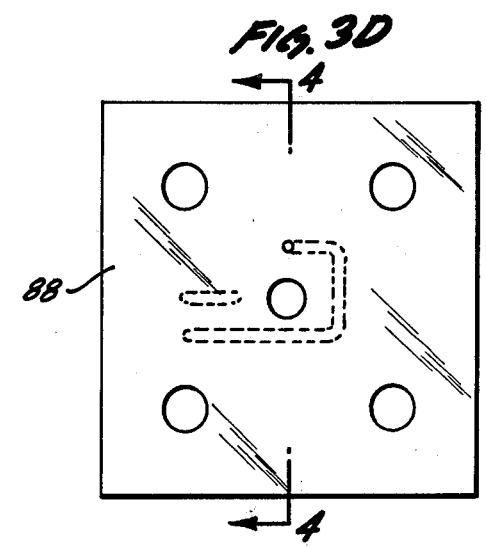
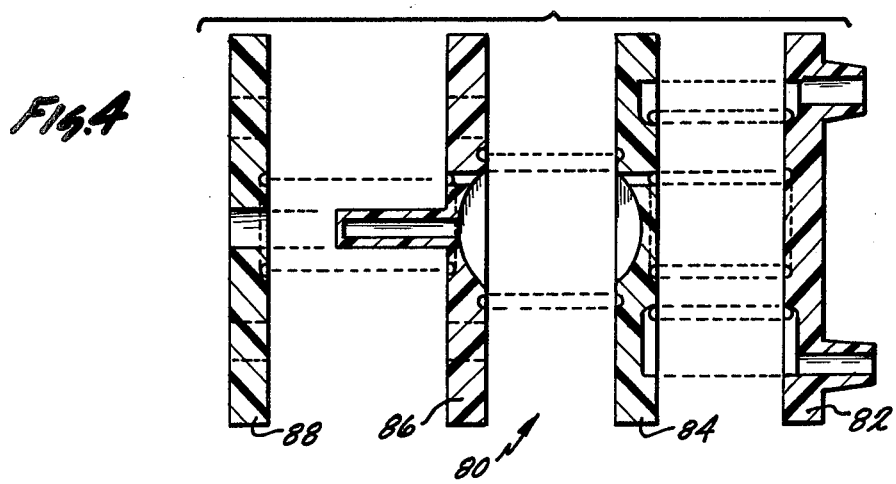

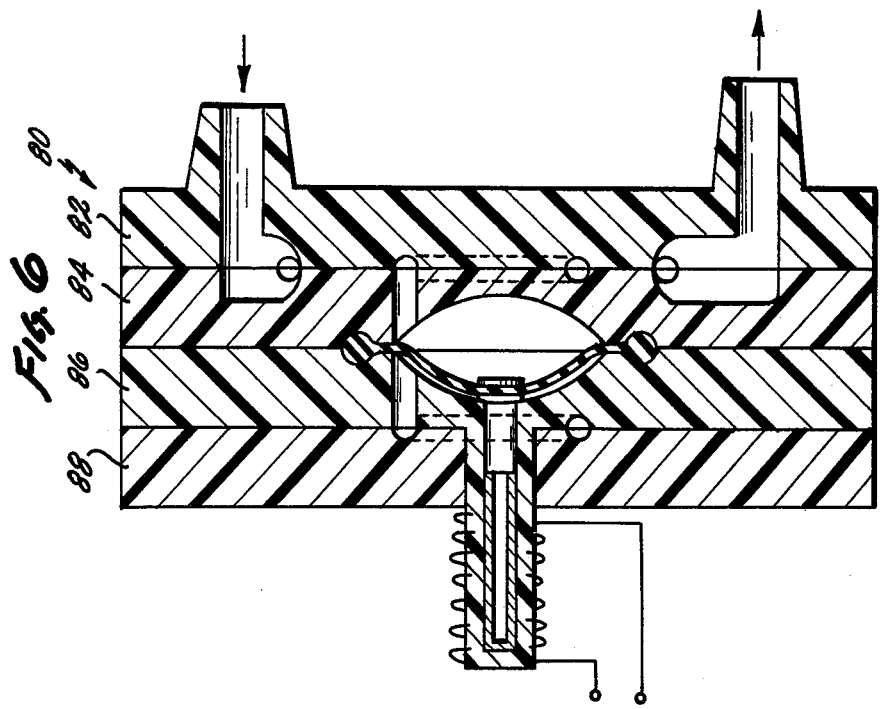
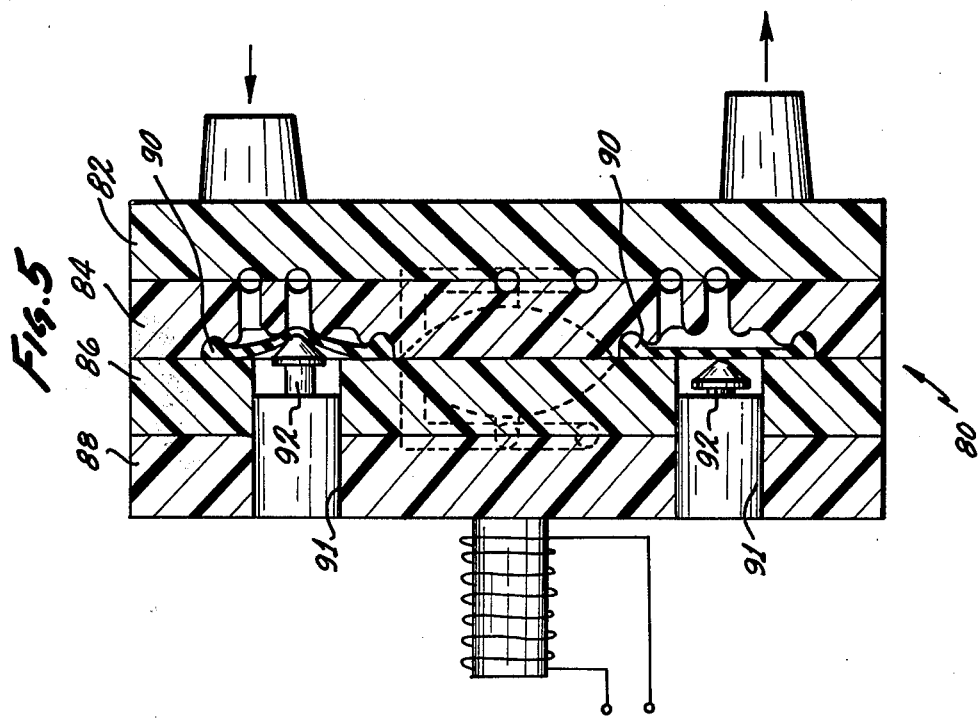

CASSETTE FOR INTRAVENOUS CONTROLLER

This invention relates to a cassette for providing for the introduction of intravenous fluid on a controlled basis into a patient. More particularly, the apparatus relates to a cassette which is used in a system to provide for the introduction of intravenous fluid into a patient and which is replaceable on a sterile and hygienic basis every time that the system is used with a different patient.

As the practice of medicine becomes increasingly complex and increasingly refined, the equipment and techniques used to provide care for a patient also have become increasingly sensitive in order to assure that the patient receives optimum care. For example, after an operation has been performed on a patient and the patient is in the recuperative state, intravenous fluid often has to be introduced to the patient. The rate of introduction of the fluid to the patient is dependent upon a number of different factors including the weight, age, sex and physical state of the patient. As the patient recovers from his illness, the rate of introduction of the intravenous fluid to the patient is adjusted to assure that the patient receives an optimum benefit from the fluid.

A considerable amount of effort has been devoted over a substantial period of time to provide a satisfactory system for controlling the rate at which fluid such as intravenous fluid is introduced to a patient. Considerable progress has been made in developing a satisfactory system for certain types of operations. For example, a system providing for the pumping of fluid on a precise volumetric basis to a patient has been disclosed and claimed in U.S. Pat. No. 3,985,133 (issued Oct. 12, 1976) which is assigned of record to the assignee of record of this application. However, a number of fundamental problems still remain in systems providing for the flow of fluid on a gravitational basis to a patient even though a considerable effort has been devoted to the solution of such problems. For example, a satisfactory system still does not exist for providing for the introduction of fluid at a precise and predetermined rate into a patient on a gravitational basis. Furthermore, a system still does not exist which can be used on a sterile and hygienic basis for different patients such that any contamination from one patient will not affect subsequent patients.

In copending application Ser. No. 913,294 filed concurrently by Jon. A. Jenkins for a "System for Controlling the Introduction of Fluid to a Patient" and assigned of record to the assignee of record of this application, a system is disclosed and claimed for providing an introduction of intravenous fluid on a precisely controlled gravitational basis to a patient. Since the fluid flows on a gravitational basis into the patient, the fluid cannot be forced into the patient. This is advantageous in insuring that the patient cannot be injured by any malfunction of the system. In a system in which fluid is pumped into the patient, such malfunctions of the system occasionally tend to force fluid into the patient under improper circumstances.

The system disclosed and claimed in application Ser. No. 913,294 is also advantageous because it provides for the use of replaceable cassettes. In this way, any previously used cassette can be discarded and a new cassette can be inserted into the system every time that the system is to be used to provide a controlled introduction of fluid to a new patient. This insures that the cassette provided for each patient will be sterile and hygienic and that the system will not have to be sterilized after each use.

This invention provides a cassette for use with the system disclosed and claimed in application Ser. No. 913,294. The cassette is advantageous because it can be easily inserted into the system for use with a different patient and can be easily removed from the system and discarded after such use. The cassette is further advantageous because it operates in conjunction with the system disclosed and claimed in application Ser. No. 913,294 to insure that the system operates on a positive and reliable basis to provide for the introduction of the fluid on a gravitational basis into a patient at a precise and predetermined rate. The cassette is further advantageous because it assures that the fluid flows from the source through the cassette to the patient without contaminating the system in any way. In this way, the system can be used for successive patients, without any necessity to sterilize the system, merely by replacing a previously used cassette with a cassette previously sterilized and not yet used.

The cassette constituting this application includes a block and a chamber in the block. Separating means such as a diaphragm are disposed in the chamber to define first and second compartments which are separated from each other. The diaphragm is movable in the chamber to define variable volumes for the first and second compartments in accordance with such movement. As the volume of one of the compartments is increased by movement of the diaphragm, the volume of the other compartment is correspondingly decreased.

A transducer is movable with the diaphragm. The transducer is constructed to indicate the position of the diaphragm in the chamber. The transducer may include a coil fixedly positioned on the block and a magnetic rod magnetically coupled to the coil and movable with the diaphragm to vary the inductance of the coil in accordance with such movement. The variable inductance of the coil is used in the system to sense the passage of fluid through the cassette to the patient so that the fluid is introduced to the patient at the precise and predetermined rate.

Input and output lines are provided in the block. First and second pairs of lines communicate with the input and output lines and with the first and second compartments in a particular relationship. For example, one of the lines in the first pair communicates with the input line and the first compartment and the other line in the first pair communicates with the second compartment and the output line. Similarly, one of the lines in the second pair communicates with the input line and the second compartment and the other line in the second pair communicates with the first compartment and the output line.

Control means such as valves are disposed in each of the lines in the first and second pairs. The valves are operated by the system in alternate relationships. For example, in one relationship, the valves provide for an opening of the first pair of lines and a blocking of the second pair of lines so that fluid flows into the first compartment from a source of intravenous fluid and simultaneously flows from the second compartment to the patient. In the other relationship, the valves provide for an opening of the second pair of lines and a blocking of the first pair of lines so that fluid flows from the source to the second compartment and simultaneously from the first compartment to the patient.

In the drawings:

FIGS. 3A through 3D are top plan views of different segments which may be separately formed and then adhered to form the cassette;

FIG. 4 is an exploded sectional view taken substantially on the line 4—4 of FIGS. 3A through 3D with the segments in position to be adhered to one another to form the cassette;

FIG. 5 is a sectional view taken substantially on the line 5—5 of FIG. 3B and illustrates the relative operations of two valves, one in open relationship or position and the other in a closed relationship or position; and FIG. 6 is a sectional view taken substantially on the line 4—4 of FIGS. 3A through 3D with the segments in assembled relationship to define the cassette.

Figure 1:
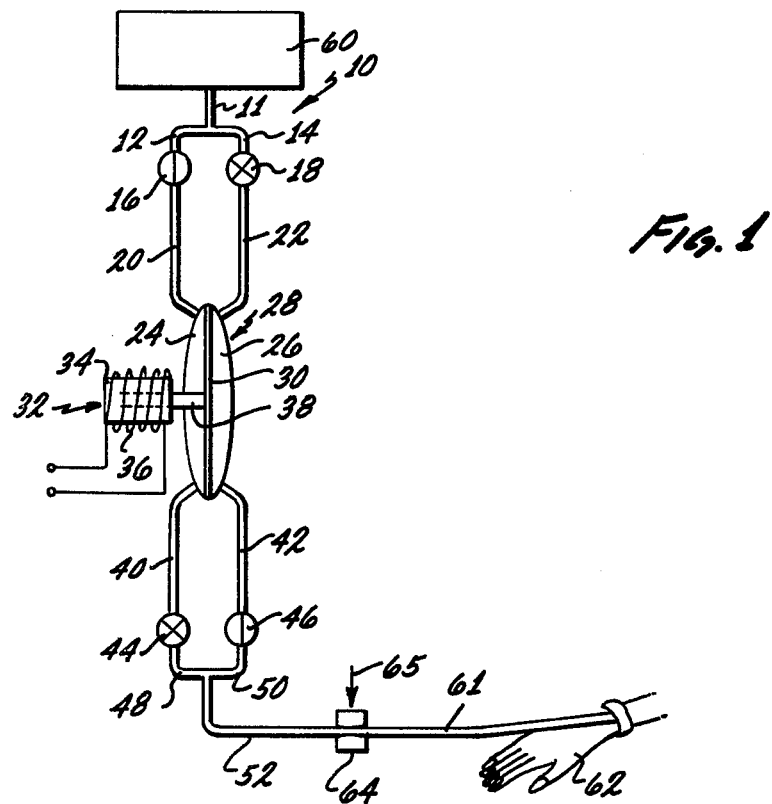
FIG. 1 is an elevational view in schematic form of the important features of a cassette constituting one embodiment of the invention.

A cassette generally indicated at 10 is shown on a schematic basis in FIG. 1. The cassette may be made from any rigid material such as a number of different plastic materials. The cassette includes an input line 11 and a pair of conduits 12 and 14 branching from the input line. Valves 16 and 18 are respectively disposed in the lines 12 and 14 and are operative in open and closed states. Branch lines 20 and 22 respectively extend from the valves 16 and 18 to first and second compartments 24 and 26 in a chamber generally indicated at 28. The compartments 24 and 26 are defined by a separating member 30 extending across the chamber. The separating member is attached at its periphery to the walls of the chamber and is movable between the end walls respectively defining the boundaries of the compartments 24 and 26. The separating means 30 may be made from a thin sheet of a resilient material such as rubber so as to constitute a diaphragm.

A transducer generally indicated at 32 is associated with the diaphragm 30 to indicate the position of the diaphragm at each instant. The transducer 32 may include a hollow bulb 34 which extends from one of the walls of the chamber 28 such as the wall defining the boundary of the compartment 24. The bulb 34 is disposed in hermetically sealed relationship to the wall of the compartment 24. The bulb 34 and the compartment 24 may be open to each other at their common boundary.

A transducer member such as a coil 36 is wound on the bulb 34. A second transducer member such as a magnetic rod 38 extends from the diaphragm 30 into the hollow confines of the bulb or tube 34 and is movable with the diaphragm. In this way, the inductance of the coil 36 can be varied in accordance with displacements of the diaphragm 30 toward the boundary wall of the compartment 26 or toward the boundary wall of the compartment 24.

Branch lines 40 and 42 respectively extend from the compartments 24 and 26. Valves 44 and 46 are respectively disposed at the ends of the branch lines 40 and 42. Each of the valves 44 and 46 is operative in open and closed states. Branch lines 48 and 50 respectively extend from the valves 44 and 46 to an output line 52.

The input line 11 is connected to a source 60 of fluid. Similarly, the output line 52 is connected to an external line 61, which extends to a patient 62 (illustrated schematically by a hand and an arm) when the cassette is in use. A pinch clamp 64 may be coupled to the line 61 to control the rate at which fluid passes to the patient. The pinch clamp 64 is adjustable to control the opening in the line 61. The adjustability of the pinch clamp 64 is illustrated by an arrow 65 in FIG. 1.

In the operation of the cassette, the valves 18 and 44 are paired and the valves 16 and 46 are paired. At any one time, one pair of valves may be open and the other pair of valves may be closed. In FIG. 1, the closed position of the valves is illustrated by an "X" in a circle and the open position of the valves is illustrated by a circle without an "X" in the circle. For example, when the valves 16 and 46 are open, the valves 18 and 44 are closed. At such a time, fluid flows downwardly from the source 60 through the lines 11 and 12, the valve 16 and the line 20 into the compartment 24. At the same time, fluid flows outwardly from the compartment 26 through the line 42, the valve 46, the line 50 and the lines 52 and 61 to the patient 62. The rate of such flow is controlled by the setting of the pinch clamp 64. Since fluid flows into the compartment 24 and out of the compartment 26, the diaphragm 30 is flexed to the right in FIG. 5. This causes the rod 38 to move outwardly from the coil 36 so that the inductance of the coil decreases.

Similarly, when the valves 16 and 46 are closed, the valves 18 and 44 are open. At such a time, fluid flows downwardly from the source 60 through the line 11, the line 14, the valve 18 and the line 22 into the compartment 26. At the same time, fluid flows outwardly from the compartment 24 to the patient 62 through the line 40, the valve 44, the line 48 and the lines 52 and 61. The rate of such flow is also controlled by the setting of the pinch clamp 64. Since fluid flows into the compartment 26 and out of the compartment 24, the diaphragm 30 is flexed to the left in FIG. 1 so that the rod 38 moves into the coil 36. This causes the inductance of the coil 36 to increase.

Figure 2:
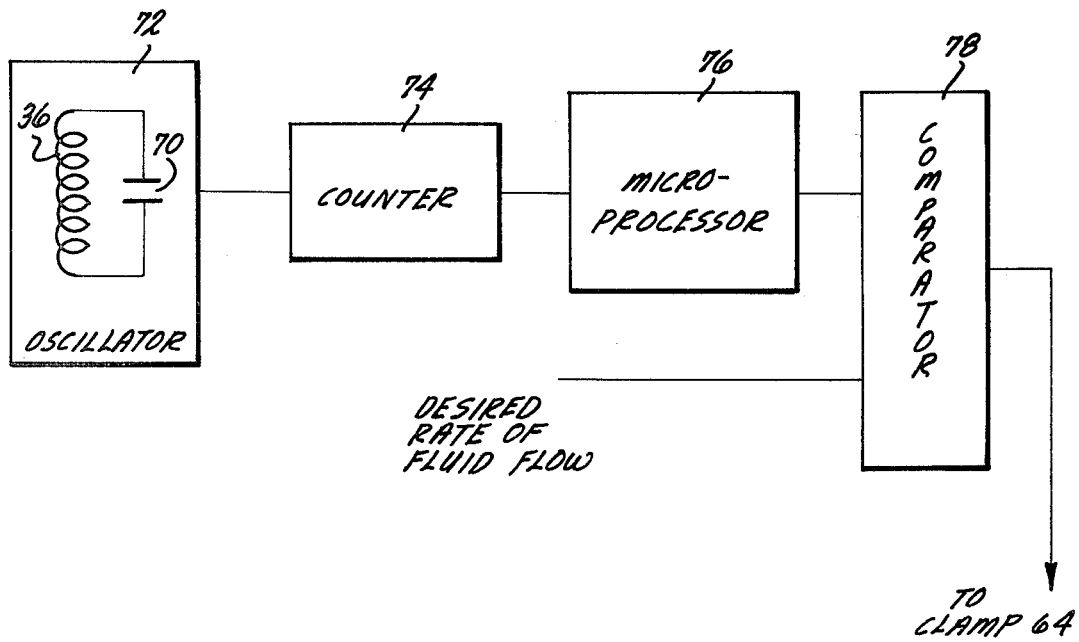
FIG. 2 is a schematic view, primarily in block form, of a system constituting a controlelr in which the cassette shown in the drawings can be used.

The cassette is included in a system schematically shown in FIG. 2. This system is fully disclosed and claimed in application Ser. No. 913,294 filed by Jon A. Jenkins on June 7, 1978 and assigned of record to the assignee of record of this application. The system shown in FIG. 6 includes the coil 36 which is connected in a parallel resonant circuit with a capacitance 70. This parallel resonant circuit is included in an oscillator 72. Since the resonant frequency of the parallel resonant circuit varies in accordance with the inductance of the coil 36, the frequency of the signals from the oscillator varies in accordance with the movements of the diaphragm 30. As a result, the frequency of the signals from the oscillator 72 provides an indication of the positioning of the diaphragm 30 in the chamber 28 at each instant. Furthermore, the signals from the oscillator 72 are introduced to a counter 74 which counts the signals from the oscillator and introduces this count to a microprocessor 76. The microprocessor 76 processes the signals from the counter 74 and differentiates these signals to provide a signal representing the actual rate at which fluid flows to the patient. These signals are compared in a comparator 78 with signals representing a desired rate of fluid flow to produce an error signal in accordance with any difference in the characteristics of the compared signals. The error signal is used to adjust the position of the clamp 64 in a direction for minimizing the error signal.

As will be seen from FIGS. 4, 5 and 6, the cassette 10 is provided in the form of a block generally indicated at 80 and made of a suitable material such as a plastic. Preferably the block 80 is formed from segments or platelets 82, 84, 86 and 88 (FIGS. 3A through 3D) of a clear plastic material such as a material designated as "Lucite" by E. I. duPont de Nemours & Company of Wilmington, Del. The lines 11, 12, 14, 20, 22, 40, 42, 50 and 52 may be formed as by etching or chemical milling in individual ones of the segments or platelets 82, 84, 86 and 88 defining the block 80. Similarly, the chamber 30 may also be formed as by etching or chemical milling appropriate cavities in the segments or platelets defining the block 80. After being suitably etched, the segments or platelets 82, 84, 86 and 88 may be adhered in stacked relationship to produce the block 80.

The valves 16, 18, 44 and 46 may be formed in any suitable manner in the block 80. For example, each of the valves may be provided with control means such as a diaphragm 90 (FIG. 5) which is variably positioned in a chamber 92. In one position of the diaphragm 90, fluid is unable to flow between the input line to the valve and the output line from the valve. In another position of the diaphragm 90, fluid is able to flow between such input and output lines. The diaphragm 90 may be normally biased to the open position and may be moved to the closed position by a plunger 92. In FIG. 5, the valve on the right is in the open position and the valve on the left is in the closed position.

Means are provided in the system disclosed and claimed in application Ser. No. 913,294 for moving the plungers 92 (and, therefore, the diaphragms 90) in synchronism with the movement of the diaphragm 30. For example, when the diaphragm 30 has moved to the end of its excursion in the direction of the wall defining the boundary of the compartment 24, the diaphragms 90 for the valves 16 and 46 moved to the closed position and the diaphragms 90 for the valves 18 and 44 are released for movement to the open position. Similarly, the diaphragms 90 for the valves 18 and 44 are moved to the closed position and the diaphragms 90 for the valves 16 and 46 are released for movement to the closed position when the diaphragm 30 has moved to the end of its excursion in the direction of the wall defining the boundary of the compartment 26.

It will be appreciated that other types of arrangements may be used for the valves 16, 18, 44 and 46 in addition to that described above. For example, each valve may include a rotary member rotatable between first and second positions. In the first rotary position, each member may provide for the passage of fluid. In the second rotary position, each member may prevent the passage of fluid. The rotary members may be movable by a reversible motor between the open and closed positions of the associated valves.

The cassette described above has certain advantages. One advantage is that it is easily formed as by injection molding various segments or platelets and then adhering the platlets in sandwiched relationship. Another advantage is that the cassette can be easily inserted into a system for controlling the flow of fluid into a patient and can be easily removed from the system. Furthermore, the cassette is isolated from the system such that fluid flows only through the cassette and not through the system. In this way, when the system is to be used to control the flow of fluid to a new patient, a previously used cassette can be replaced by a cassette which has been previously sterilized at the time of manufacture and which has been retained in sterilized form. The use of such a previously sterilized cassette assumes that the patient undergoing treatment will not be contaminated by any previous patient.

The cassette disclosed above has other advantages of some importance. For example, the cassette provides a controlled storage of fluid from the source in accordance with the adjustments in the clamp 64. This results from the fact that fluid flows into one of the compartments in the chamber 28 only in accordance with the flow of fluid from the other compartment in the chamber and fluid flows from the chamber only in accordance with the flow of fluid through a line 61. Thus, the chamber 28 in the cassette serves as a reservoir whose operation is controlled by adjustable clamp 64.

The cassette is also advantageous in other respects. It includes as a separate entity the chamber 28, the transducer 32 and the valves 16, 18, 44 and 46. Thus, all of the members controlling the flow of fluid through the cassette, except for the adjustable clamp 64, are included in the cassette. This causes the cassette to be essentially a self-sufficient unit in providing a controlled flow of fluid from the source 60 to the patient. Furthermore, since the clamp 64 is external to the line 61 and does not contact the fluid in the line, the only elements contacting the fluid and controlling the flow of fluid are in the cassette.

The cassette also has other advantages over the prior art. For example, the hydrostatic pressure in the source of the intravenous fluid is produced at the cassette. This hydrostatic pressure is created by the height of the source of intravenous fluid above the cassette. The transmission of the hydrostatic pressure from the source to the cassette results in part from the provision of two compartments in the cassette. If the cassette had only a single compartment, hydrostatic pressure would be transmitted only from the cassette to the patient.

Although this application has been disclosed and illustrated with reference to particular applications, the principles involved are susceptible of numerous other applications which will be apparent to persons skilled in the art. The invention is, therefore, to be limited only as indicated by the scope of the appended claims.

I claim:

1. In combination in a cassette for providing for a controlled introduction of fluid from a source to a patient,
   a block,
   a chamber disposed in the block,
   a flexible diaphragm disposed in the chamber and separating this chamber into first and second compartments each having a variable volume in accordance with the flexing of the diaphragm,
   a transducer operatively coupled to the diaphragm for movement with the diaphragm and extending from the diaphragm in sealed relationship with the chamber,
   an input line in the block for receiving fluid from the source,
   an output line in the block for providing for the introduction of fluid to the patient,
   a first pair of lines in the block, one of the lines in the first pair providing a communication between the input line and the first compartment and the other one of the lines in the pair providing a communication between the output line and the second compartment, and
   a second pair of lines in the block, one of the lines in the second pair providing a communication between the input line and the second compartment and the other one of the lines in the second pair providing a communication between the output line and the first compartment, and control means disposed in cooperative relationship with the first and second pair of lines for providing alternately for a blocking of the second pair of lines and an opening of the first pair of lines and for providing at other times for a blocking of the first pair of lines and an opening of the second pair of lines.

2. In the combination set forth in claim 1, the transducer including a rod made from a magnetizable material and disposed within a tube extending from the block and further including a coil wound on the tube in magnetically coupled relationship to the rod.

3. In the combination set forth in claim 1, the control means including a first pair of valves for the first pair of lines and a second paid of valves for the second pair of lines.

4. In the combination set forth in claim 1, each of the valves in the first and second pairs having first and second operative relationships and being operative in the first relationship to provide for a flow of fluid through the associated line and being operative in the second relationship to block the flow of fluid through the associated line and each of the valves including control means for providing a controlled operation of the first and second valves in the first and second operative relationships.

5. A cassette for use in an intravenous controller providing for a controlled introduction of fluid between a source and a patient, including, a block, a chamber disposed in the block, a flexible diaphragm disposed in the chamber and dividing the chamber into first and second compartments, an input line, an output line, first means disposed in the block for providing for an introduction of fluid on a controlled basis into either one of the compartments from the input line and a flow of fluid from the other compartment into the output line and for providing for a flexing of the diaphragm in accordance with the flow of fluid into the one compartment and the flow of fluid from the other compartment, and second means disposed in the block for alternately providing for an introduction of fluid into the first compartment from the input line and a flow of fluid from the second compartment into the output line and for providing for a flexing of the diaphragm in the direction of the second compartment in accordance with the flow of fluid into the first compartment and the flow of fluid from the second compartment and for providing at the other times for an introduction of fluid into the second compartment from the input line and a flow of fluid from the first compartment into the output line and for providing for a flexing of the diaphragm in the direction of the first compartment in accordance with the flow of fluid into the second compartment and the flow of fluid from the first compartment, and third means cooperative with the diaphragm for providing an indication of the position of the diaphragm.

6. In the combination set forth in claim 5, the first means including first and second lines respectively extending from the input line to the first and second compartments and third and fourth lines respectively extending from the first and second compartments to the output line.

7. In the combination set forth in claim 6, the second means including first, second, third and fourth valves such disposed in a respective one of the first, second, third and fourth lines and each having first and second operative relationships and operative in the first relationship to open the associated line for the flow of fluid through the line and operative in the second relationship to close the associated line against the flow of fluid through the line.

8. In the combination set forth in claim 7, the third means including first transducer means disposed on the member in a stationary relationship and second transducer means disposed in variably coupled relationship with the first transducer means and movable with the diaphragm into individual positions of coupling with the first transducer means to provide an indication of the position of the diaphragm in accordance with such individual positions of coupling.

9. In the combination set forth in claim 8, the first transducer means including a coil and the second transducer means including a magnetic rod disposed in magnetically coupled relationship to the coil.

10. A cassette for use in an intravenous controller providing for a controlled introduction of fluid between a source and a patient, including, a block, a chamber formed in the block, a movable member disposed in the chamber and dividing the chamber into first and second compartments each having a volume variable in accordance with the movements of the movable member, a first pair of valves disposed in the block, each of the valves in the first pair being operable in open and closed relationships and including a member movable between a first position providing for an open relationship and a second position providing for a closed relationship, a second pair of valves disposed in the block, each of the valves in the second pair being operable in open and closed relationships and including a member movable between a first position providing for an open relationship and a second position providing for a closed relationship, an input line communicating at one end with a particular one of the valves in the first and second pairs and providing for communication with the source of fluid at the other end, an output line communicating at one end with the other one of the vaves in the first and second pairs and providing for communication with the patient at the other end, a first conduit providing a communication between the particular value in the first pair and the first compartment, a second conduit providing a communication between the other valve in the first pair and the second compartment, a third conduit providing a communication between the first valve in the second pair and the second compartment, a fourth conduit providing a communication between the other valve in the second pair and the first compartment, and transducer means associated with the movable member for indicating the positioning of the movable member in the chamber.

11. The cassette of claim 10, including, the transducer means including the first means disposed on the block and second means disposed in coupled relationship with the first means and movable with the movable member for providing a variably coupled relationship with the first means in accordance with such movement and for providing for a variable indication in accordance with such variable coupling.

12. The cassette set forth in claim 11 wherein the first means includes a coil and the second means includes a magnetic rod disposed in magnetically coupled relationship to the coil and movable relative to the coil to provide a variable magnetic coupling with the coil.

13. The cassette of claim 11 wherein each of the valves in the first and second pairs has first and second operative relationships and is operative in the first relationship to provide for a passage of fluid through the associated lines and is operative in the second relationship to prevent a passage of fluid through the associated lines.

14. In combination in a cassette for providing for a controlled introduction of fluid from a source to a patient, a block, a chamber disposed in the block and defined by first and second opposite walls, separating means extending across the chamber and defining a first compartment with the first wall and a second compartment with the second wall and movable between the first and second walls to provide the first compartment and the second compartment with variable volumes in an inverse relationship to each other, transducer means disposed on the block and responsive to movements of the separating means for providing an indication at each instant of the position of the separating means between the first and second walls of the chamber, first means disposed in the block for providing for an independent communication between the source and each of the compartments, second means disposed in the block for providing for an independent communication between each of the compartments and the patient, and valve means associated with the first and second means for providing for a flow of fluid from the first means into the first compartment and a flow of fluid from the second compartment to the second means and for providing for a flow of fluid from the first means to the second compartment and for providing for a flow of fluid from the first compartment to the second means.

15. The combination set forth in claim 14 wherein the valve means are provided with first and second operative relationships and are operative in the first relationship to provide for a flow of fluid into the first compartment and out of the second compartment and are operative in the second relationship to provide for a flow of fluid into the second compartment and out of the first compartment.

16. The combination set forth in claim 15 wherein first and second pairs of valve means are provided and wherein one of the first and second pairs of valve means is operative at any one time in the first relationship and the other pair of valve means is operative at the same time in the second relationship and the first pair of valve means is operative in the first relationship to provide for a flow of fluid into the first compartment and out of the second compartment and the second pair of valve means is operative in the first relationship to provide for the flow of fluid into the second compartment and out of the first compartment.

17. The combination set forth in claim 15 wherein a bulb is disposed on the block in communication with the chamber and first transducing means are disposed on the bulb and second transducing means are disposed within the bulb in cooperative relationship with the first transducing means to provide a variable impedance in accordance with variations in its positioning relative to the first transducing means and wherein the second transducing means is movable with the separating means in the chamber.

18. The combination set forth in claim 17 wherein the first transducing means is a coil and the second transducing means is a rod having magnetizable properties and the separating means is a diaphragm.

* * * * *